United States Patent
Wang et al.

(10) Patent No.: US 6,992,151 B2
(45) Date of Patent: Jan. 31, 2006

(54) PHOSPHORUS-CONTAINING FLAME-RETARDANT HARDENER, AND EPOXY RESINS CURED BY THE SAME

(75) Inventors: Chun-Shan Wang, Tainan (TW); Jeng-Yueh Shieh, Tainan (TW)

(73) Assignee: National Science Council, Taipei (TW)

( * ) Notice: Subject to any disclaimer, the term of this patent is extended or adjusted under 35 U.S.C. 154(b) by 363 days.

(21) Appl. No.: 10/618,915

(22) Filed: Jul. 14, 2003

(65) Prior Publication Data

US 2004/0024255 A1    Feb. 5, 2004

Related U.S. Application Data

(62) Division of application No. 09/571,682, filed on May 16, 2000, now Pat. No. 6,613,848.

(30) Foreign Application Priority Data

Jan. 4, 2000    (TW) ................. 889100075

(51) Int. Cl.
C08G 59/62    (2006.01)
C08L 63/02    (2006.01)
C08L 63/04    (2006.01)

(52) U.S. Cl. ............ 525/480; 525/481; 525/485; 525/486; 525/496; 525/497; 525/504; 525/523; 525/533

(58) Field of Classification Search ........... 525/480, 525/481, 496, 497, 504, 485, 486, 523, 533; 528/129, 149, 150, 158, 163; 564/15, 16; 558/17, 76, 82
See application file for complete search history.

(56) References Cited

U.S. PATENT DOCUMENTS 6,180,695 B1 *    1/2001   Ito et al. .............. 523/451

6,291,626 B1 *    9/2001   Wang et al. ........... 528/99

FOREIGN PATENT DOCUMENTS

JP    63-19254 A2 *   1/1988
JP    04300968 A      10/1992

OTHER PUBLICATIONS

Chun-Shan Wang and Jeng-Yueh Shieh, "Synthesis and Properties of Epoxy Resins Containing 2-(6-oxid-6H-dibenz (c,e)(1,2)oxaphosphorin-6-yl)1,4-benzenediol," Polymer, Nov. 1998, vol. 38, No. 23, pp. 5819-5826.*

Chun-Shan Wang and Jeng-Yueh Shieh, "Synthesis and Properties of Epoxy Resins Containing 2-(6-oxid-6H-dibenz (c,e)(1,2) oxaphosphorin-6-yl) 1,4-benzenediol, " Polymer vol. 39, No. 23, pp. 5819-5826, Nov. 1998.

* cited by examiner

*Primary Examiner*—Robert Sellers
(74) *Attorney, Agent, or Firm*—Jackson Walker L.L.P.

(57)    ABSTRACT

The present invention discloses an active-hydrogen-containing curing agent having a phosphorus group, and a flame retardant cured epoxy resin which can be prepared via an addition reaction between the active hydrogen and the epoxide group of an epoxy resin. The cured flame retardant epoxy resin is environmentally friendly and is suitable for printed circuit board and semiconductor encapsulation applications. The phosphorus group of the curing agent has a chemical structure as follows:

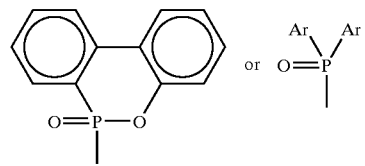

wherein Ar is a substituted or un-substituted phenyl or phenoxy.

14 Claims, No Drawings

PHOSPHORUS-CONTAINING FLAME-RETARDANT HARDENER, AND EPOXY RESINS CURED BY THE SAME

This application is a divisional of application Ser. No. 09/571,682 filed May 16, 2000, U.S. Pat. No. 6,613,848, which claims the priority of Taiwanese patent application No. 089100075, filed Jan. 4, 2000, the content of which are hereby incorporated by reference.

FIELD OF THE INVENTION

The present invention relates generally to an active-hydrogen-containing phosphorus compound for cross-linking a resin and for imparting flame-retardancy to the cured resin, and in particular to a cured frame-retardant epoxy resin prepared by reacting the hardener with a di- or polyfunctional epoxy resin via an addition reaction between the active hydrogen and the epoxide group.

BACKGROUND OF THE INVENTION

Epoxy resins have the excellent characteristics of moisture, solvent and chemical resistance, toughness, low shrinkage on cure, superior electrical and mechanical resistance properties, and good adhesion to many substrates. The versatility in formulation also make epoxy resins widely applicable industrially for surface coatings, adhesive, painting materials, potting, composites, laminates, encapsulants for semiconductors, and insulating materials for electric devices, etc. o-Cresol formaldehyde novolac epoxy (CNE) is the resin typically employed in the encapsulation of microelectronic devices. Several approaches for modification of epoxy backbone for enhancing the thermal properties of epoxy resins have been reported. Aromatic bromine compounds in conjunction with antimony oxide are widely used as a flame retardant for epoxy resins. Tetrabromobisphenol A is a typical example of the aromatic bromine compounds used as a flame retardant for epoxy resins. An excess amount of epoxy resin is reacted with tetrabromobisphenol A to prepare an advanced epoxy resin having two terminal epoxide groups, as shown in the following formula:

wherein Ep is a bi-radical group of the backbone of the epoxy resin, and m is an integer of 1–10. The advanced epoxy resin can be used in preparing a flame-retardant printed circuit board (FR-4) by impregnating glass fibers with the advanced epoxy resin and heating the resulting composite to cure the advanced epoxy resin. Furthermore, the advanced epoxy resin can be employed to encapsulate microelectronic devices, in which the advanced epoxy resin is cured at a high temperature with a curing agent, so that an encapsulant having a flame-retardant property is formed. Typical examples can be found in U.S. Pat. No. 3,040,495 (1961); U.S. Pat. No. 3,058,946 (1962); U.S. Pat. No. 3,294,742 (1966); U.S. Pat. No. 3,929,908 (1975); U.S. Pat. No. 3,956,403 (1976); U.S. Pat. No. 3,974,235 (1976); U.S. Pat. No. 3,989,531 (1976); U.S. Pat. No. 4,058,507 (1997); U.S. Pat. No. 4,104,257 (1978); U.S. Pat. No. 4,170,711 (1979); and U.S. Pat. No. 4,647,648(1987)].

Although the tetrabromobisphenol A-containing advanced epoxy resin shows flame retardant property, major problems encountered with this system are concerned with the generation of toxic and corrosive fumes during combustion such as dioxin and benzofuran.

The flame retardant having a small molecular weight tends to lower the mechanical properties of the epoxy resins, and migrate/vaporize from the epoxy resins such that the flame retardancy thereof diminishes.

The trend of electronics equipment is being miniaturized and becoming thinner, at the same time the scale of integration of large scale integrated circuits (LSICs) is continuing upward, forcing the design toward larger chips, finer patterns, and higher pin counts that are more susceptible to a high-temperature failure. The prevailing surface mount technology (SMT) also causes the devices being subjected to a high temperature. Therefore, the development of a high-temperature reliable, flame-retardant and environmentally friendly epoxy resin for printed circuit board and encapsulant are essential for semiconductor industry.

It is an object of this invention to provide a phosphorus-containing flame retardant hardener for cross-linking a resin and for imparting flame-retardancy to the cured resin.

It is another object of this invention to provide cured epoxy resins with good thermal stability, superior heat resistance, and without environmental problem, which are

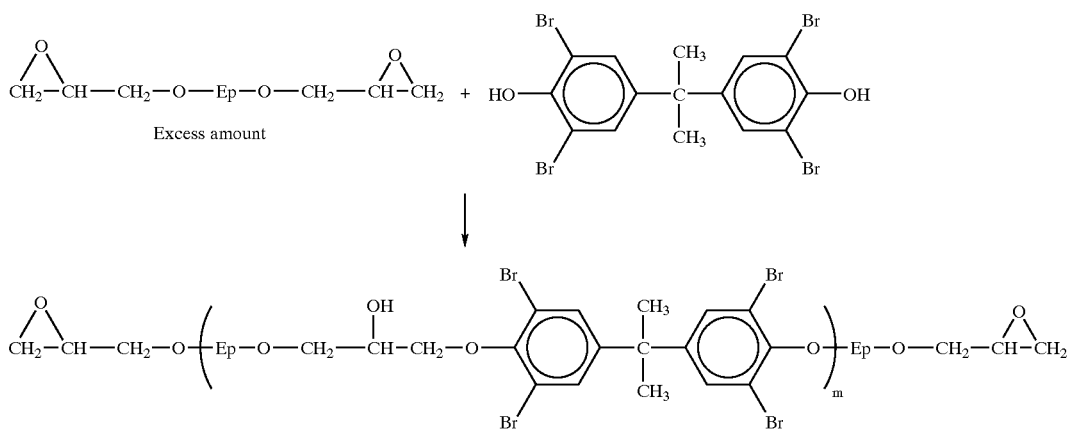

A flame retardant advanced epoxy resin

SUMMARY OF THE INVENTION

In order to accomplish the aforesaid objects, a flame-retardant hardener containing one of the following phosphorus groups was synthesized in the prevent invention:

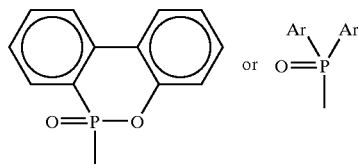

wherein Ar is an un-substituted or substituted phenyl or phenoxy radical. The hardener of the present invention is prepared by bounding the phosphorus-containing rigid group to a multi-active-hydrogen-containing compound or resin.

The present invention also provides a cured flame-retardant epoxy resin by using the hardener of the present invention. The cured flame-retardant epoxy resin so prepared has a high glass transition temperature (Tg), high decomposition temperature and high elastic modulus, and is free of toxic and corrosive fumes during combustion, and thus is suitable for printed circuit board and semiconductor encapsulation applications.

DETAILED DESCRIPTION OF THE INVENTION

A phosphorus-containing hardener prepared in accordance with the present invention has a formula selecting from the group consisting of (a), (b), (c) and (d):

(a)
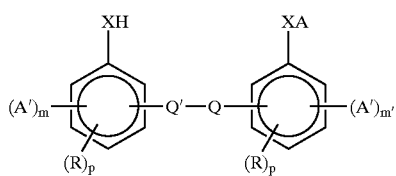

(b)
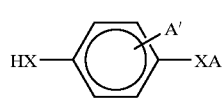

(c)
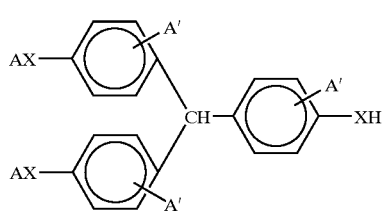

(d)
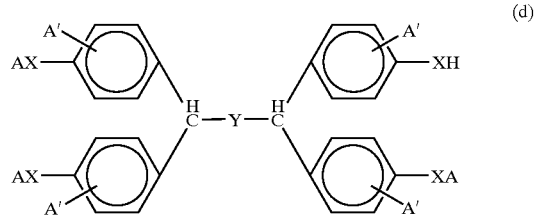

wherein
m = 1 or 2; m' = 0 or 1; p = 0~3; R = C1~C4 alkyl or aryl; X = O, S or NH;

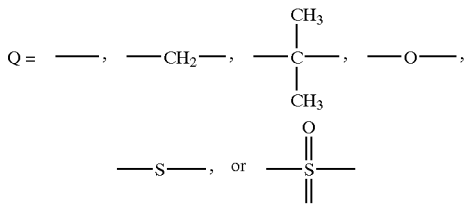

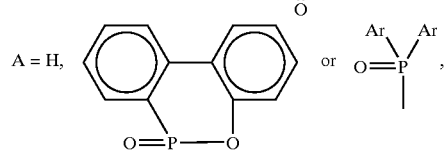

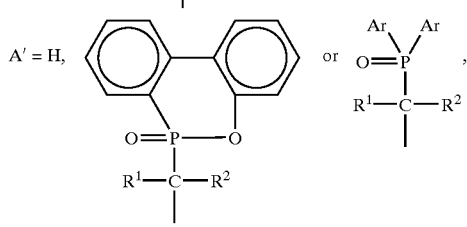

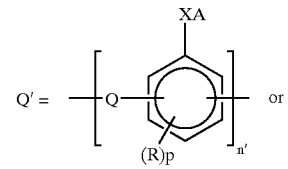

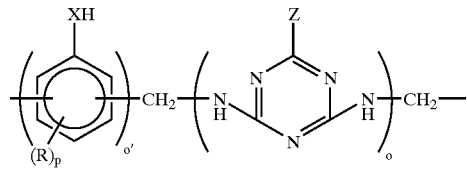

wherein Q = ——, wherein Q' is the latter;

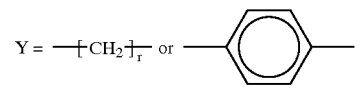

wherein $R^1$, $R^2$ independently are H, C1~C18 alkyl, C6~C18 aryl, C6~C18 substituted aryl, C6~C18 aryl methylene, or C6~C18 substituted aryl methylene;

n'=0~11; Z=—$NH_2$, —NHR, or —R; o=1~3; o'=3~10; r=0~6; R, Q and p are defined as above;

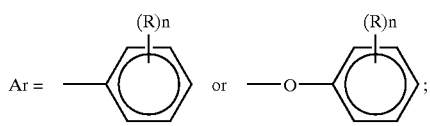

wherein R and r are defined as above;

wherein either all the A or all the A' in each formula of (a) to (d) are H, and at least one of the A is not H when all the A' are H in each formula of (a) to (d), and at least one of the A' is not H when all the A are H in each formula of (a) to (d).

Preferably, R is hydrogen or methyl, and more preferably R is hydrogen.

Preferably, Q=—CH$_2$— or

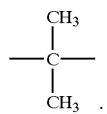

Preferably, X is —O— or —NH—. More preferably, X is —O—.

Preferably, Y is —, i.e. r is 0.

Preferably, the hardener of the present invention has a structure of the formula (a).

Preferably, the hardener of the present invention has a structure of the formula (b).

Preferably, the hardener of the present invention has a structure of the formula (c).

Preferably, the hardener of the present invention has a structure of the formula (d).

Preferably, all the A' are H, and

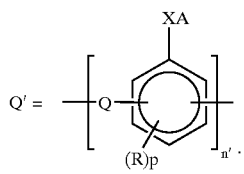

More preferably, only one A is not H.

Preferably, all the A are H, and only one A' is not H.

Preferably, all the A are H, and

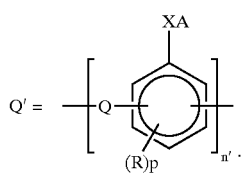

Preferably, all the A are H, and Q' is

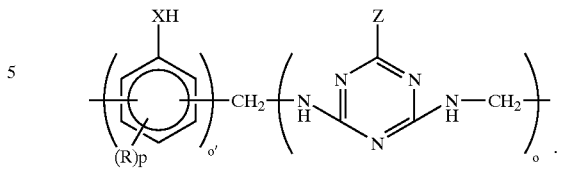

More preferably, Z is —NH$_2$.

Preferably, $R^1$—C—$R^2$ is one of the followings:

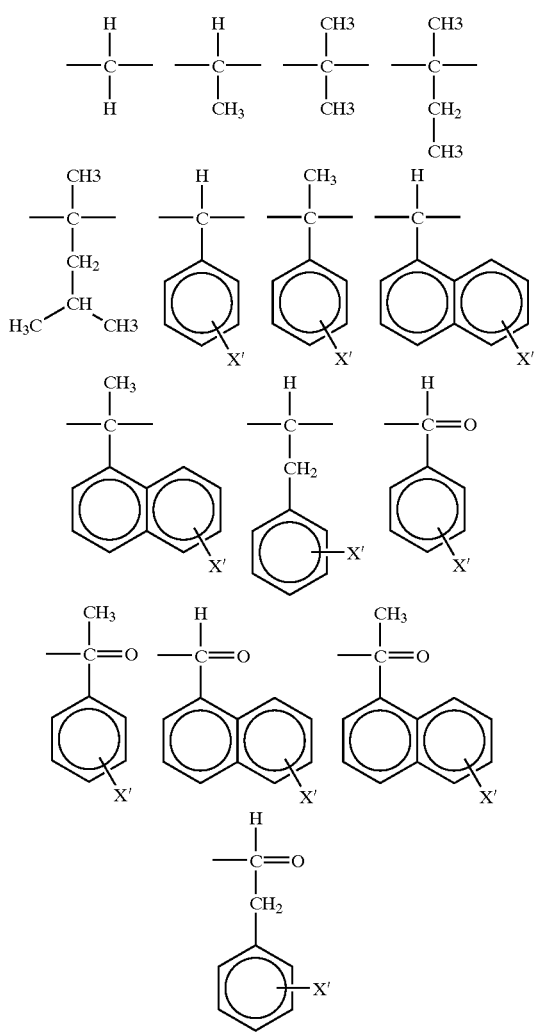

wherein X'=H or halogen. More preferably, $R^1$ and $R^2$ are hydrogen.

The hardener of the present invention can be synthesized by bounding a reactive phosphorus-containing rigid group to a multi-active-hydrogen-containing compound or resin. There are two different schemes for preparing the hardener of the present invention depending on the types of the reactants containing the reactive phosphorus-containing rigid group. The reactants having the following formulas (I) or (II) are used to prepare the hardener having all the A in the formulas (a) to (d) being hydrogen:

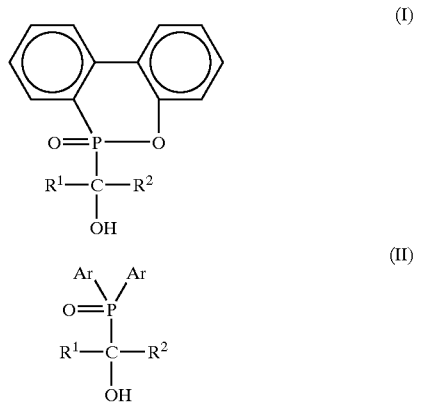

(I)

(II)

by reacting with a multi-active-hydrogen-containing compound or resin having a structure selected from the formulas (III) to (VII) as follows:

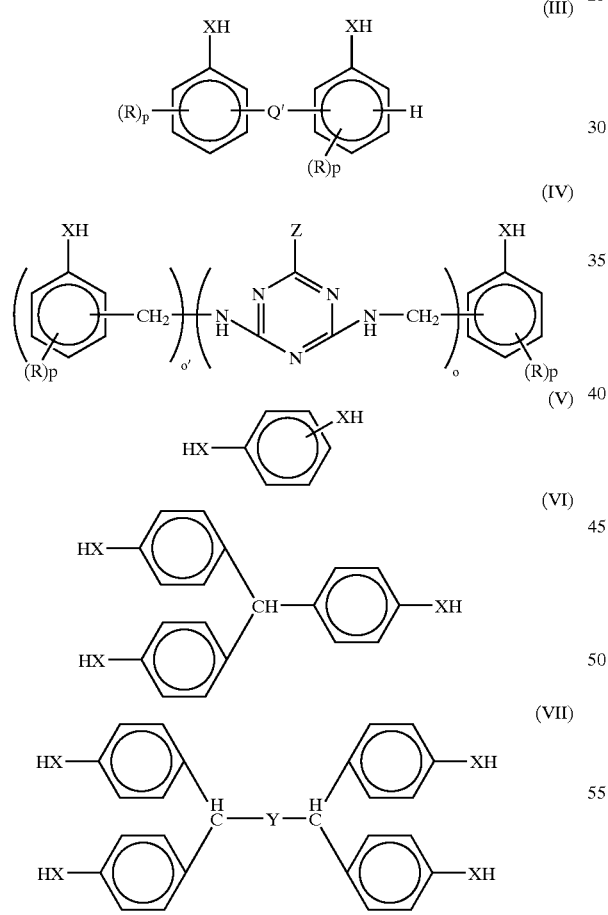

(III)

(IV)

(V)

(VI)

(VII)

wherein $R^1$, $R^2$, Ar, R, Q', X, Z, Y, p, o and o' in (I) to (VII) are defined the same as above.

The reactants having the following formulas (I') or (II') are used to prepare the hardener having all the A in the formulas (a) to (d) being hydrogen:

(I')

(II')

by reacting with a multi-active-hydrogen-containing compound or resin having a structure selected from the formulas (III), (V), (VI) and (VII), wherein Ar in the formula (II') is defined as above.

The compound (I) may be synthesized by reacting 9,10-dihydro-9-oxa-10-phosphaphenanthrene 10-oxide (DOPO) with a compound of $R^1CR^2O$, as shown by the following reaction formula (VIII):

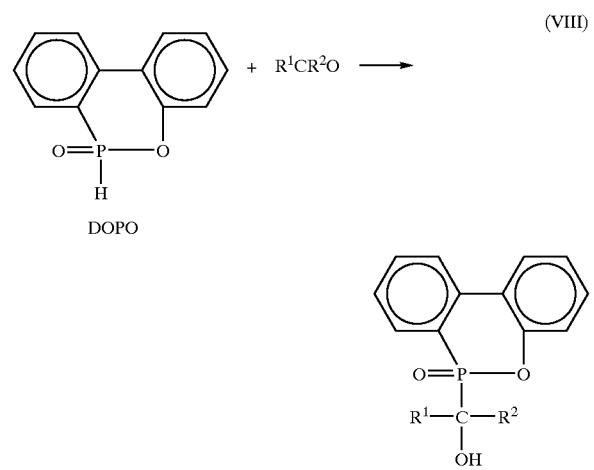

(VIII)

The compound (II) may be synthesized by carrying out a reaction as shown by the following reaction formula (IX):

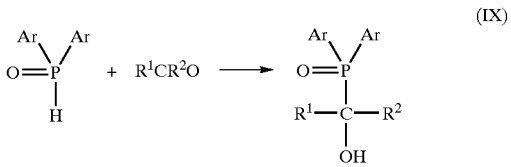

(IX)

$R^1$, $R^2$, and Ar in the formulas (VIII) and (IX) are defined as above.

A reaction suitable for synthesizing the phosphorus-containing halide, 2-(6-oxid-6H-dibenz<c,e><1,2>oxa-phosphorin-6-yl) chloride [ODOPC; (I')], is shown as follows (X):

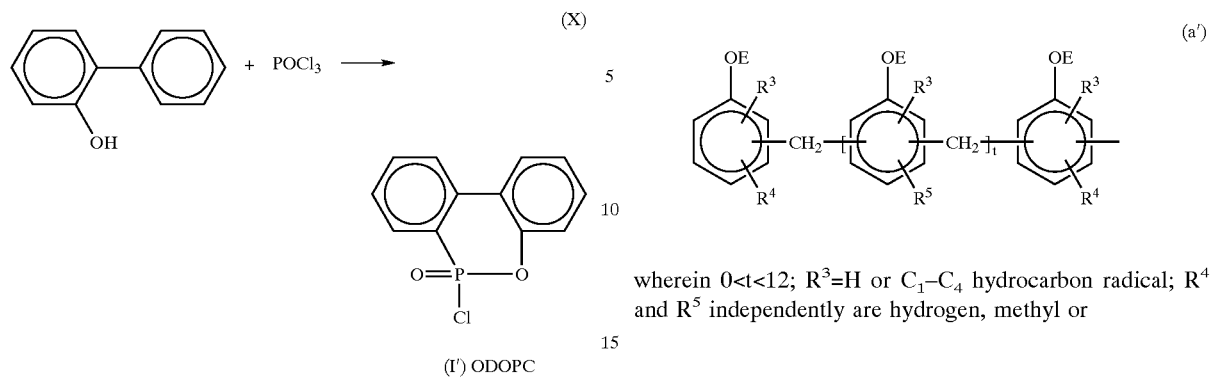

(X)

(I') ODOPC

A reaction suitable for synthesizing the phosphorus-containing halide (II'), is shown as follows (XI):

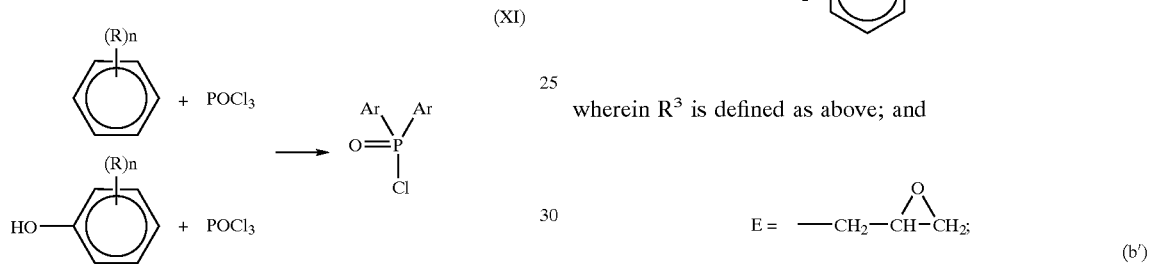

(XI)

wherein R, n and Ar are defined as above.

The present invention further synthesized a phosphorus-containing flame-retardant cured epoxy resin by curing an epoxy resin or advanced epoxy resin with the hardener of the present invention alone or together with a curing agent for an epoxy resin in a molten state. The curing agent can be any curing agent used in the art for curing an epoxy resin, and preferably is selected from the group consisting of phenol-formaldehyde novolac, dicyandiamide, methylenedianiline, diaminodiphenyl sulfone, phthalic anhydride and hexahydrophthalic anhydride. Preferably, the curing reaction is carried out at a temperature higher than 150° C. and with a stoichiometric amount of the hardener and the curing agent, i.e. the equivalent ratio of the epoxide group in the epoxy resin and/or advance epoxy resin and the functional groups in the hardener and the curing agent is about 1:1. More preferably, the curing reaction is carried out in the presence of a curing promoter such as triphenylphosphine, and in an amount of 0.01–10.0 parts by weight of the curing promoter per 100 parts by weight of the epoxy resin and/or advance epoxy resin. The phosphorus-containing flame-retardant cured epoxy resin of the present invention is suitable for use in making a flame-retardant printed circuit. board as a matrix resin and in semiconductor encapsulation.

A suitable epoxy resin for use in the present invention can be any known epoxy resin, for examples those having two epoxide groups such as bisphenol A epoxy resin, bisphenol F epoxy resin, bisphenol S epoxy resin and biphenol epoxy resin, and those having more than two epoxide groups such as phenol formaldehyde novolac epoxy and cresol formaldehyde novolac epoxy (CNE) with 4–18 functional groups, and mixtures thereof, for examples, those having the formulas (a') to (d') as follows:

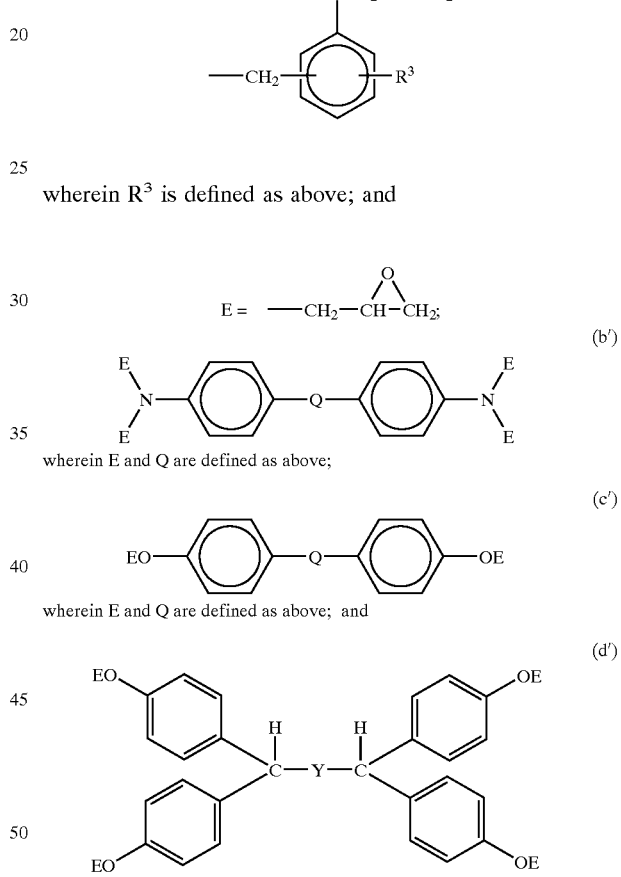

wherein $0<t<12$; $R^3$=H or $C_1$–$C_4$ hydrocarbon radical; $R^4$ and $R^5$ independently are hydrogen, methyl or wherein $R^3$ is defined as above; and $$E = \ —CH_2-CH-CH_2;$$

wherein E and Q are defined as above;

wherein E and Q are defined as above; and wherein E and Y are defined as above.

An advanced epoxy resin suitable for use in the present invention can be prepared by conducting a curing reaction of a conventional curing agent for an epoxy resin and using an excess amount of an epoxy resin in a molten state.

In synthesizing the phosphorus-containing flame-retardant cured epoxy resin, the active hydrogen of the hardener of the present invention, —XH in the formulas (a) to (d), reacts with the epoxide groups of the epoxy resin or advanced epoxy resin., Taking the hardener having a structure of the formula (c) as an example, the curing reaction can be shown as follows:

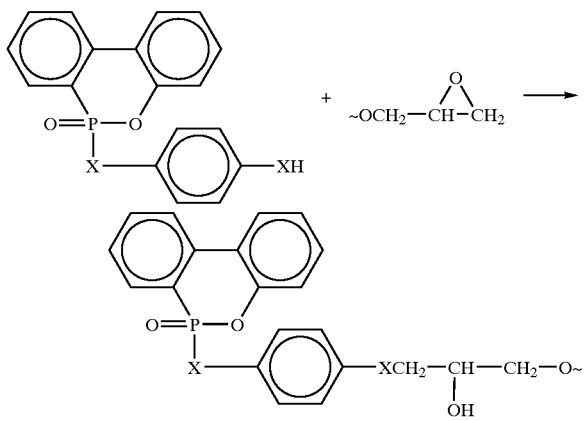

The present invention can be further understood with the help of the following examples, which are merely for description not for limiting the scope of the present invention.

I. Preparation of Phosphorus-containing Alcohol (Preparation Examples 1–9) and Phosphorus-containing Chloride (Preparation Examples 10–11)

Preparation Example 1

To a one liter four-inlet flask equipped with a temperature controller, a reflux condenser, a nitrogen feed and a mechanical stirrer, 1 mole (216 g) of 9,10-dihydro-9-oxa-10-phosphaphenanthrene-10-oxide (DOPO, purchased from TCI Co.) and 500 ml xylene were added. The mixture was heated to 50° C. and then stirred. The mixture was heated to a temperature of 90° C. and the stirring was continued until DOPO was dissolved completely. To this solution was added slowly 1.0 mole (30 g) formaldehyde within one hour, and the temperature thereof was increased to 110–115° C. and maintained at that temperature for four hours after the addition of formaldehyde was completed. The mixture was then cooled to room temperature, filtered, and purified with tetrahydrofuran (THF) to obtain 2-(6-oxido-6H-dibenz<c,e><1,2>oxa-phosphorin 6-yl) methanol [ODOPM; (I)]. Yield, 92%; m.p. 152–154° C. Anal. Calcd. for $C_{13}H_{11}PO_3$: C, 63.41; H, 4.47; O, 19.51; P, 12.61. Found: C, 63.32; H, 4.51; O, 18.93; P, 13.24. EIMS, m/z: 251 (96. $M^+$)

Preparation Example 2

To a one liter four-inlet flask equipped with a temperature controller, a reflux condenser, a nitrogen feed and a mechanical stirrer, 1 mole (216 g) DOPO and 500 ml THF were added. The mixture was heated to 50° C. and then stirred. The mixture was heated to a temperature of 70° C. and the stirring was continued until DOPO was dissolved completely. To this solution was added slowly 1.0 mole (58 g) acetone within two hours, and the temperature thereof was increased to 70° C. and maintained at that temperature for four hours after the addition of acetone was completed. The mixture was then cooled to room temperature to obtain white solid, which was then filtered, and purified with THF to yield 2-[2-(6-oxid-6H-dibenz<c,e><1,2>oxa-phosphorin-6-yl)]propan-2-ol [ODOPP; (I)]. Yield, 96%; m.p. 128–130° C. Anal. Calcd. for $C_{15}H_{15}PO_3$: C, 65.69; H, 5.47; O 17.52; P, 11.32. Found: C, 65.61; H, 5.52; O, 17.36; P, 11.51. EIMS, m/z: 274 (92. $M^+$).

Preparation Example 3

To a one liter four-inlet flask equipped with a temperature controller, a reflux condenser, a nitrogen feed and a mechanical stirrer, 1 mole (216 g) DOPO and 500 ml p-chloro nitrobenzene were added. The mixture was heated to 50° C. and then stirred. The mixture was heated to a temperature of 90° C. and the stirring was continued until DOPO was dissolved completely. To this solution was added slowly 1.0 mole (72 g) 2-butanone within two hours, and the temperature thereof was increased to 120–125° C. and maintained at that temperature for six hours after the addition of 2-butanone was completed. The mixture was then cooled to room temperature to obtain white solid, which was then filtered, and purified with THF to yield 2-[2-(6-oxid-6H-dibenz<c,e><1,2>oxa-phosphorin-6-yl)]butan-2-ol [ODOPB; (I)]. Yield, 92%; m.p. 101–103° C. Anal. Calcd. for $C_{16}H_{17}PO_3$: C, 66.67; H, 5.90; O, 16.66; P, 10.77. Found: C, 66.59; H, 5.97; O, 16.45; P, 10.99. EIMS, m/z: 288 (96. $M^+$).

Preparation Example 4

To a one liter four-inlet flask equipped with a temperature controller, a reflux condenser, a nitrogen feed and a mechanical stirrer, 1 mole (234 g) diphenyl phosphite (DPP) and 500 ml xylene were added. The mixture was heated to 70° C. and then stirred. The mixture was heated to a temperature of 90° C. and the stirring was continued until DPP was dissolved completely. To this solution was added slowly 1.0 mole (30 g) formaldehyde within two hours, and the temperature thereof was increased to 138° C. and maintained at that temperature for four hours after the addition of formaldehyde was completed. The mixture was then cooled to room temperature to obtain solid, which was then filtered, and purified with THF to yield diphenoxy phosphoryl methanol [DPOM; (II)]. Yield, 96%; m.p. 72~96° C. Anal. Calcd. for $C_{13}H_{13}PO_4$: C, 59.10; H, 4.92; O, 24.24; P, 11.74. Found: C, 59.01; H, 4.98; O, 23.64; P, 12.37. EIMS, m/z: 264 (92. $M^+$).

Preparation Example 5

To a one liter four-inlet flask equipped with a temperature controller, a reflux condenser, a nitrogen feed and a mechanical stirrer, 1 mole (234 g) diphenyl phosphite (DPP) and 500 ml THF were added. The mixture was heated to 50° C. and then stirred. The mixture was heated to a temperature of 90° C. and the stirring was continued until DPP was dissolved completely. To this solution was added slowly 1.0 mole (58 g) acetone within two hours, and the temperature thereof was increased to 70° C. and maintained at that temperature for four hours after the addition of acetone was completed. The mixture was then cooled to room temperature to obtain solid, which was then filtered, and purified with THF to yield 2-(diphenoxy phosphoryl) propan-2-ol [DPOP; (II)]. Yield, 96%; m.p. 70–72° C. Anal. Calcd. for $C_{15}H_{17}PO_4$: C, 61.64; H, 5.82; O, 21.92; P, 10.62. Found: C, 61.52; H, 5.96; O, 21.78; P, 10.74. EIMS, m/z: 292 (92. $M^+$).

Preparation Example 6

To a one liter four-inlet flask equipped with a temperature controller, a reflux condenser, a nitrogen feed and a mechanical stirrer, 1 mole (234 g) diphenyl phosphite (DPP) and 500 ml xylene were added. The mixture was heated to 70° C. and then stirred. The mixture was heated to a temperature of 90° C. and the stirring was continued until DPP was dissolved completely. To this solution was added slowly 1.0 mole (72 g) 2-butanone within two hours, and the temperature thereof was increased to 120–1258° C. and maintained at that temperature for six hours after the addition of 2-butanone was completed. The mixture was then cooled to room temperature to obtain solid, which was then filtered, and purified with THF to yield 2-(diphenoxy phosphoryl) butan-2-ol methanol [DPOB; (II)]. Yield, 96%; m.p. 52–54° C. Anal. Calcd. for $C_{16}H_{19}PO_4$: C, 62.75; H, 6.21; O, 20.91; P, 10.13. Found: C, 62.61; H, 6.27; O, 20.81; P, 10.31. EIMS, m/z: 306 (92. M$^+$).

Preparation Example 7

To a one liter four-inlet flask equipped with a temperature controller, a reflux condenser, a nitrogen feed and a mechanical stirrer, 1 mole (202 g) diphenyl phosphine oxide (DPPO) and 500 ml xylene were added. The mixture was heated to 70° C. and then stirred. The mixture was heated to a temperature of 90° C. and the stirring was continued until DPPO was dissolved completely. To this solution was added slowly 1.0 mole (30 g) formaldehyde within two hours, and the temperature thereof was increased to 138° C. and maintained at that temperature for six hours after the addition of formaldehyde was completed. The mixture was then cooled to room temperature to obtain solid, which was then filtered, and purified with THF to yield diphenyl phosphoryl methanol [DPPM; (II)]. Yield, 96%; m.p. 121–123° C. Anal. Calcd. for $C_{13}H_{13}PO_2$: C, 67.24; H, 5.60; O, 13.79; P, 13.36. Found: C, 67.08; H, 5.68; O, 13.59; P, 13.65. EIMS, m/z: 232 (94. M$^+$).

Preparation Example 8

To a one liter four-inlet flask equipped with a temperature controller, a reflux condenser, a nitrogen feed and a mechanical stirrer, 1 mole (202 g) diphenyl phosphine oxide (DPPO) and 500 ml THF were added. The mixture was heated to 70° C. and then stirred. The stirring was continued until DPPO was dissolved completely. To this solution was added slowly 1.0 mole (58 g) acetone within two hours, and the temperature thereof was maintained at 70° C. for six hours after the addition of acetone was completed. The mixture was then cooled to room temperature to obtain solid, which was then filtered, and purified with THF to yield 2-(diphenyl phosphoryl) propan-2-ol [DPPP]. Yield, 96%; m.p. 96–98° C. Anal. Calcd. for $C_{15}H_{17}PO_2$: C, 69.23; H, 6.53; O, 12.31; P, 11.93. Found: C, 69.11; H, 6.63; O, 12.18; P, 12.08. EIMS, m/z: 260 (96. M$^+$).

Preparation Example 9

To a one liter four-inlet flask equipped with a temperature controller, a reflux condenser, a nitrogen feed and a mechanical stirrer, 1 mole (202 g) diphenyl phosphine oxide (DPPO) and 500 ml xylene were added. The mixture was heated to 70° C. and then stirred. The mixture was heated to a temperature of 90° C. and the stirring was continued until DPPO was dissolved completely. To this solution was added slowly 1.0 mole (72 g) 2-butanone within two hours, and the temperature thereof was increased to 120–125° C and maintained at that temperature for eight hours after the addition of 2-butanone was completed. The mixture was then cooled to room temperature to obtain solid, which was then filtered, and purified with THF to yield 2-(diphenyl phosphoryl) butan-2-ol [DPPB; (II)]. Yield, 94%; m.p. 81–83° C. Anal. Calcd. for $C_{16}H_{19}PO_2$: C, 70.07; H, 6.93; O, 11.68; P, 11.32. found: C, 69.68; H, 6.98; O, 11.46; P, 11.88. EIMS, m/z: 274 (94. M$^+$).

Preparation Example 10

To a one liter four-inlet flask equipped with a temperature controller, a reflux condenser, a nitrogen feed and a mechanical stirrer, 1 mole (170 g) o-phenyl phenol (PP) and 500 ml p-chloro nitrobenzene were added. The mixture was heated to 50° C. and then stirred. The mixture was heated to a temperature of 90° C. and the stirring was continued until PP was dissolved completely. To this solution was added slowly 1.5 mole (230 g) phosphoryl chloride ($POCl_3$) within two hours. The evolution of HCl gas was detected immediately. The temperature was increased to 110–115° C. and maintained at that temperature for six hours after the addition of $POCl_3$ was completed. HCl evolution subsided. After the addition of 3.0 g $ZnCl_2$, the mixture was further heated to 192–196° C. for eight hours. The mixture was then cooled to room temperature and purified with dichloromethane to yield liquid 2-(6-oxid-6H-dibenz<c,e><1,2>oxa-phosphorin-6-yl) chloride [ODOPC; (I')]. Yield, 93%. The IR spectrum (KBr) exhibited absorption at 1186, 1292 cm$^{-1}$ (P=O); 1172, 962 cm$^{-1}$ (P—O—P h); 1462, 1424 cm$^{-1}$ (P—Ph). Anal. Calcd for $C_{12}H_8PO_2Cl$: C, 57.48; H, 3.19; O, 12.77; P, 12.38; Cl, 14.17. Found: C, 57.52; H, 3.15; O, 12.65; P, 12.30; Cl, 14.38. EIMS, m/z: 251 (92, M$^+$).

Preparation Example 11

To a one liter four-inlet flask equipped with a temperature controller, a reflux condenser, a nitrogen feed and a mechanical stirrer, 2 moles (188 g) phenol and 500 ml N,N-dimethyl acetamide (DMAc) were added. The mixture was heated to 70° C. and then stirred. The mixture was heated to a temperature of 90° C. and the stirring was continued until phenol was dissolved completely. To this solution was added slowly 1.5 mole (230 g) phosphoryl chloride ($POCl_3$) within two hours. The evolution of HCl gas was detected immediately. The temperature was increased to 135–138° C. and maintained at the reflux temperature for 12 hours after the addition of $POCl_3$ was completed. HCl evolution subsided. The mixture was then cooled to room temperature and purified with dichloromethane to yield liquid diphenoxy phosphoryl chloride [DPOC; (II')]. Yield, 96%. Anal. Calcd. for $C_{12}H_{10}PO_3Cl$: C, 53.53; H, 3.72; O, 17.84; P, 11.52; Cl, 13.28. Found: C, 53.49; H, 3.70; O, 17.64; P, 11.64; Cl, 13.53. EIMS, m/z: 251 (90. M$^+$).

II. Preparation of Phosphorus-containing Hardeners

Preparation Example 12 (P-1, ODOPM-PN)

To a one liter four-inlet flask equipped with a thermocouple and temperature controller, a reflux condenser, a nitrogen feed and a mechanical stirrer, 1 mole (624 g) phenol novolac resin (PN) and 500 ml toluene were added. The mixture was heated to 70° C. and then stirred. The mixture was heated to a temperature of 90° C. and the stirring was continued until PN was dissolved completely. To this solution was added slowly 1.0 mole (246 g) ODOPM. The temperature was increased to 140° C. and maintained at that temperature for 12 hours after the addition of ODOPM was completed. The mixture was then cooled to room temperature, filtered and dried to obtain ODOPM-PN (P-1). Yield, 98%; softening temperature, 67–75° C. Phosphorus content: 3.64%.

Preparation Example 13 (P-2, ODOPM-MPN)

To a one liter four-inlet flask equipped with a thermocouple and temperature controller, a reflux condenser, a nitrogen feed and a mechanical stirrer, 1 mole (609 g) melamine-phenol novolac resin (MPN) and 500 ml toluene were added. The mixture was heated to 90° C. and then stirred. The mixture was heated to a temperature of 120° C. and the stirring was continued until MPN was dissolved completely. To this solution was added slowly 1.0 mole (246 g) ODOPM. The temperature was increased to 140° C. and maintained at that temperature for 10 hours after the addition of ODOPM was completed. The mixture was then cooled to room temperature, filtered and dried to obtain ODOPM-MPN (P-2). Yield, 98%; softening temperature, 117–125° C. Phosphorus content: 3.63%; nitrogen content: 9.82%.

Preparation Example 14 (P-3, ODOPM-THPE)

To a one liter four-inlet flask equipped with a thermocouple and temperature controller, a reflux condenser, a nitrogen feed and a mechanical stirrer, 1 mole (398 g) of 1,1,2,2,tetrakis(4-hydroxy phenyl) ethane)phenol resin (THPE) and 500 ml toluene were added. The mixture was heated to 70° C. and then stirred. The stirring was continued until THPE was dissolved completely. To this solution was added slowly 1.0 mole (246 g) ODOPM. The temperature was increased to 120° C. and maintained at that temperature for 8 hours after the addition of ODOPM was completed. The mixture was then cooled to room temperature, filtered and dried to obtain ODOPM-THPE (P-3). Yield, 94%; softening temperature, 122–127° C. Phosphorus content: 5.09%.

Preparation Example 15 (P-4, ODOPM-THPM)

To a one liter four-inlet flask equipped with a thermocouple and temperature controller, a reflux condenser, a nitrogen feed and a mechanical stirrer, 1 mole (292 g) of tri-hydroxy phenyl methane resin (THPM) and 500 ml toluene were added. The mixture was heated to 70° C. and then stirred. The stirring was continued until THPM was dissolved completely. To this solution was added slowly 1.0 mole (246 g) ODOPM. The temperature was increased to 120° C. and maintained at that temperature for 8 hours after the addition of ODOPM was completed. The mixture was then cooled to room temperature, filtered and dried to obtain ODOPM-THPM (P-4). Yield, 96%; softening temperature, 103–105° C. Phosphorus content: 6.18%.

Preparation Example 16 (P-5, ODOPM-PD)

To a one liter four-inlet flask equipped with a thermocouple and temperature controller, a reflux condenser, a nitrogen feed and a mechanical stirrer, 1 mole (108 g) of p-phenylene diamine resin (PD) and 500 ml DMAc were added. The mixture was cooled to −5° C. after PD was dissolved completely. To this solution was added slowly 1.0 mole (246 g) ODOPM. The resulting mixture was maintained at −5° C. for 6 hours after the addition of ODOPM was completed, and then at room temperature for another 4 hours. The mixture was cooled to 0° C., filtered and dried to obtain ODOPM-PD (P-5). Yield, 94%; softening temperature, 137–139° C. Phosphorus content: 9.75%.

Preparation Example 17 (P-6, ODOPM-DDM)

To a one liter four-inlet flask equipped with a thermocouple and temperature controller, a reflux condenser, a nitrogen feed and a mechanical stirrer, 1 mole (198 g) of diaminodiphenyl methane resin (DDM) and 500 ml DMAc were added. The mixture was heated to 50° C. and then stirred. The mixture was heated to a temperature of 90° C. and the stirring was continued until DDM was dissolved completely. To this solution was added slowly 1.0 mole (246 g) ODOPM. The temperature was increased to 130° C. and maintained at that temperature for 6 hours after the addition of ODOPM was completed. The mixture was then cooled to room temperature, filtered and dried to obtain ODOPM-DDM (P-6). Yield, 97%; softening temperature, 121–123° C. Phosphorus content: 7.58%.

Preparation Example 18 (P-7, DPPM-PN)

To a one liter four-inlet flask equipped with a thermocouple and temperature controller, a reflux condenser, a nitrogen feed and a mechanical stirrer, 1 mole (624 g) phenol novolac resin (PN) and 500 ml toluene were added. The mixture was heated to 70° C. and then stirred. The mixture was heated to a temperature of 90° C. and the stirring was continued until PN was dissolved completely. To this solution was added slowly 1.0 mole (248 g) diphenyl phosphoryl methanol (DPPM). The temperature was increased to 120° C. and maintained at that temperature for 6 hours after the addition of DPPM was completed. The mixture was then cooled to room temperature, filtered and dried to obtain DPPM-PN (P-7). Yield, 97%; softening temperature, 48–52° C. Phosphorus content: 3.56%.

Preparation Example 19 (P-8, DPPM-MPN)

To a one liter four-inlet flask equipped with a thermocouple and temperature controller, a reflux condenser, a nitrogen feed and a mechanical stirrer, 1 mole (609 g) melamine-phenol novolac resin (MPN) and 500 ml toluene were added. The mixture was heated to. 70° C. and then stirred. The mixture was heated to a temperature of 90° C. and the stirring was continued until MPN was dissolved completely. To this solution was added slowly 1.0 mole (248 g) diphenyl phosphoryl methanol (DPPM). The temperature was increased to 120° C. and maintained at that temperature for 6 hours after the addition of DPPM was completed. The mixture was then cooled to room temperature, filtered and dried to obtain DPPM-MPN (P-8). Yield, 97%; softening temperature, 59–65° C. Phosphorus content:. 3.61%; nitrogen content: 9.8%.

Preparation Example 20 (P-9, DPOM-PN)

To a one liter four-inlet flask equipped with a thermocouple and temperature controller, a reflux condenser, a nitrogen feed and a mechanical stirrer, 1 mole (624 g) phenol novolac resin (PN) and 500 ml toluene were added. The mixture was heated to 70° C. and then stirred. The mixture was heated to a temperature of 90° C. and the stirring was continued until PN was dissolved completely. To this solution was added slowly 1.0 mole (264 g) diphenoxy phosphoryl methanol (DPOM). The temperature was increased to 120° C. and maintained at that temperature for 6 hours after the addition of DPOM was completed. The mixture was then cooled to room temperature, filtered and dried to obtain DPOM-PN (P-9). Yield, 98%; softening temperature, 63–68° C. Phosphorus content: 3.49%.

Preparation Example 21 (P-10, DPOM-MPN)

To a one liter four-inlet flask equipped with a thermocouple and temperature controller, a reflux condenser, a nitrogen feed and a mechanical stirrer, 1 mole (609 g) melamine-phenol novolac resin (MPN) and 500 ml toluene were added. The mixture was heated to 70° C. and then stirred. The mixture was heated to a temperature of 90° C. and the stirring was continued until MPN was dissolved completely. To this solution was added slowly 1.0 mole (246 g) diphenoxy phosphoryl methanol (DPOM). The temperature was increased to 120° C. and maintained at that temperature for 8 hours after the addition of DPOM was completed. The mixture was then cooled to room temperature, filtered and dried to obtain DPOM-MPN (P-10). Yield, 98%; softening temperature, 79–83° C. Phosphorus content: 3.63%; nitrogen content: 9.8%.

Preparation Example 22 (P'-1, ODOPC-PN)

To a one liter four-inlet flask equipped with a thermocouple and temperature controller, a reflux condenser, a nitrogen feed and a mechanical stirrer, 1 mole (648 g) phenol novolac resin (PN) and 500 ml toluene were added. The mixture was heated to 70° C. and then stirred. The mixture was heated to a temperature of 90° C. and the stirring was continued until PN was dissolved completely. To this solution was added slowly 1.0 mole (251 g) 2-(6-oxid-6H-dibenz<c,e><1,2>oxa-phosphorin-6-yl) chloride (ODOPC). The temperature was increased to 140° C. and maintained at that temperature for 6 hours after the addition of ODOPC was completed. The mixture was then cooled to room temperature, filtered and dried to obtain ODOPC-PN (P'-1). Yield, 98%; softening temperature, 67–75° C. Phosphorus content: 3.64%.

Preparation Example 23 (P'-3, ODOPC-THPE)

To a one liter four-inlet flask equipped with a thermocouple and temperature controller, a reflux condenser, a nitrogen feed and a mechanical stirrer, 1 mole (398 g) 1,1,2,2,tetrakis(4-hydroxy phenyl) ethane)phenol resin (THPE) and 500 ml toluene were added. The mixture was heated to 70° C. and then stirred. The stirring was continued until THPE was dissolved completely. To this solution was added slowly 1.0 mole (251 g) 2-(6-oxid-6H-dibenz<c,e><1,2>oxa-phosphorin-6-yl) chloride (ODOPC). The temperature was increased to 100° C. and maintained at that temperature for 8 hours after the addition of ODOPC was completed. The mixture was then cooled to room temperature, filtered and dried to obtain ODOPC-THPE (P'-3). Yield, 94%; softening temperature, 122–127° C. Phosphorus content: 5.06%.

Preparation Example 24 (P'-4, ODOPC-THPM)

To a one liter four-inlet flask equipped with a thermocouple and temperature controller, a reflux condenser, a nitrogen feed and a mechanical stirrer, 1 mole (292 g) tri-hydroxyl phenyl methane (THPM) and 500 ml toluene were added. The mixture was heated to 70° C. and then stirred. The stirring was continued until THPM was dissolved completely. To this solution was added slowly 1.0 mole (251 g) 2-(6-oxid-6H-dibenz<c,e><1,2>oxa-phosphorin-6-yl) chloride (ODOPC). The temperature was increased to 120° C. and maintained at that temperature for 8 hours after the addition of ODOPC Was completed. The mixture was then cooled to room temperature, filtered and dried to obtain ODOPC-THPM (P'-4). Yield, 96%; softening temperature, 118–124° C. Phosphorus content: 6.12%.

Preparation Example 25 (P'-5, ODOPC-PD)

To a one liter four-inlet flask equipped with a thermocouple and temperature controller, a reflux condenser, a nitrogen feed and a mechanical stirrer, 1 mole (108 g) of p-phenylene diamine resin (PD) and 500 ml DMAc were added. The mixture was cooled to −15° C. after PD was dissolved completely. To this solution was added slowly 1.0 mole (251 g) ODOPC. The resulting mixture was maintained at −15° C. for 6 hours after the addition of ODOPC was completed, and then at room temperature for another 4 hours. The mixture was cooled to 0° C., filtered and dried to obtain ODOPC-PD (P'-5). Yield, 94%; m.p. 153–155° C. Phosphorus content: 9.61%.

Preparation Example 26 (P'-6, ODOPC-DDM)

To a one liter four-inlet flask equipped with a thermocouple and temperature controller, a reflux condenser, a nitrogen feed and a mechanical stirrer, 1 mole (198 g) diamidodiphenyl methane resin (DDM) and 500 ml DMAc were added. The mixture was heated to 50° C. and then stirred. The mixture was heated to a temperature of 90° C. and the stirring was continued until DDM was dissolved completely. To this solution was added slowly 1.0 mole (251 g) 2-(6-oxid-6H-dibenz<c,e><1,2>oxa-phosphorin-6-yl) chloride (ODOPC). The temperature was increased to 130° C. and maintained at that temperature for 2 hours after the addition of ODOPC was completed. The mixture was then cooled to room temperature, filtered and dried to obtain ODOPC-DDM (P'-6). Yield, 96%; m.p. 136–138° C. Phosphorus content: 7.52%.

Preparation Example 27 (P'-7, DPC-PN)

To a one liter four-inlet flask equipped with a thermocouple and temperature controller, a reflux condenser, a nitrogen feed and a mechanical stirrer, 1 mole (648 g) phenol novolac resin (PN) and 500 ml toluene were added. The mixture was heated to 70° C. and then stirred. The mixture was heated to a temperature of 90° C. and the stirring was continued until PN was dissolved completely. To this solution was added slowly 1.0 mole (253 g) diphenyl phosphoryl chloride (DPC). The temperature was increased to 120° C. and maintained at that temperature for 6 hours after the addition of DPC was completed. The mixture was then cooled to room temperature, filtered and dried to obtain DPC-PN (P'-7). Yield, 96%; softening temperature, 113–117° C. Phosphorus content: 4.32%.

Preparation Example 28 (P'-9, DPOC-PN)

To a one liter four-inlet flask equipped with a thermocouple and temperature controller, a reflux condenser, a nitrogen feed and a mechanical stirrer, 1 mole (648 g) phenol novolac resin (PN) and 500 ml toluene were added. The mixture was heated to 70° C. and then stirred. The mixture was heated to a temperature of 90° C. and the stirring was continued until PN was dissolved completely. To this solution was added slowly 1.0 mole (269 g) diphenoxy phosphory chloride (DPOC). The temperature was increased to 120° C. and maintained at that temperature for 6 hours after the addition of DPOC was completed. The mixture was then cooled to room temperature, filtered and dried to obtain DPOC-PN (P'-9). Yield, 98%; softening temperature, 93–97° C. Phosphorus content: 4.06%.

III. Curing of Epoxy Resins With the Phosphorus-containing Hardeners

EXAMPLES 1–10

Cured epoxy resins were prepared from a cresol formaldehyde novolac epoxy resin (CNE) with the hardeners P-1 to P-10 prepared in Preparation Examples 12 to 21 in a 1:1 equivalent ratio and with 0.2 wt % of triphenylphosphine as a curing accelerator. The mixture was grounded into fine powders to give thermosettable epoxy resin powders. The resin powders were cured in a mold at 150° C. and 50 kg/cm² for a period of one hour and then at 170° C. for two hours and further postcured at 200° C. for three hours to obtain cured specimens.

Control Example 1

The procedures of Example 1 were repeated except that ODOPM-PN (P-1) used in Example 1 was replaced by phenol formaldehyde novolac resin (PN) to cure the cresol formaldehyde novolac epoxy resin (CNE) in the curing reaction.

Control Example 2

The procedures of Example 2 were repeated except that ODOPM-MPN (P-2) used in Example 2 was replaced by melamine-phenol formaldehyde novolac resin (MPN) to cure the cresol formaldehyde novolac epoxy resin (CNE) in the curing reaction.

Control Example 3

The procedures of Example 1 were repeated except that ODOPM-PN (P-1) used in Example 1 was replaced by tetrabromobisphenol A (TBBA) to cure the cresol formaldehyde novolac epoxy resin (CNE) in the curing reaction.

The dynamic mechanical analysis (DMA) properties of the resulting cured epoxy resins are shown in Table 1; the thermogravimetric analysis data thereof are shown in Table 2; and the flame-retardant properties thereof are shown in Table 3.

TABLE 1

| | | DMA properties | |
|---|---|---|---|
| Specimens | Hardener | Glass transition temperature (Tg, ° C.) | Flexural strength at 50° C. dyne/cm |
| Example 1 | P-1 | 183 | 7.4 |
| Example 2 | P-2 | 196 | 7.8 |
| Example 3 | P-3 | 177 | 7.5 |
| Example 4 | P-4 | 173 | 7.3 |
| Example 5 | P-5 | 174 | 7.1 |
| Example 6 | P-6 | 170 | 7.5 |
| Example 7 | P-7 | 173 | 7.0 |
| Example 8 | P-8 | 187 | 7.6 |
| Example 9 | P-9 | 171 | 6.5 |
| Example 10 | P-10 | 185 | 7.0 |
| Control Ex. 1 | PN | 167 | 6.8 |
| Control Ex. 2 | MPN | 181 | 7.1 |
| Control Ex. 3 | TBBA | 113 | 6.1 |

TABLE 2

| | | TGA data | | |
|---|---|---|---|---|
| Specimens | Hardener | Td 5% ° C. | Maximum thermal degradation temperature ° C. | Char yield (%) at 700° C. |
| Example 1 | P-1 | 383 | 427 | 47 |
| Example 2 | P-2 | 409 | 457 | 49 |
| Example 3 | P-3 | 371 | 387 | 46 |
| Example 4 | P-4 | 365 | 389 | 42 |
| Example 5 | P-5 | 334 | 378 | 36 |
| Example 6 | P-6 | 347 | 389 | 37 |
| Example 7 | P-7 | 273 | 413 | 40 |
| Example 8 | P-8 | 307 | 435 | 30 |
| Example 9 | P-9 | 367 | 411 | 39 |
| Example 10 | P-10 | 392 | 447 | 42 |
| Control Ex. 1 | PN | 417 | 479 | 30 |
| Control Ex. 2 | MPN | 429 | 497 | 35 |
| Control Ex. 3 | TBBA | 387 | 407 | 38 |

TABLE 3

| | | Flame retardant properties (UL-94 test) | | | | |
|---|---|---|---|---|---|---|
| Specimens | Hardener | Content of P or Br | Burning time Sec | Drip | Fume | Classification |
| Example 1 | P-1 | P 1.75% | 0 | No | No | V-0 |
| Example 2 | P-2 | P 1.73% | 0 | No | No | V-0 |
| Example 3 | P-3 | P 2.80% | 0 | No | No | V-0 |
| Example 4 | P-4 | P 3.58% | 0 | No | No | V-0 |
| Example 5 | P-5 | P 3.61% | 0 | No | No | V-0 |
| Example 6 | P-6 | P 3.22% | 0 | No | No | V-0 |
| Example 7 | P-7 | P 2.23% | 0 | No | No | V-0 |
| Example 8 | P-8 | P 1.72% | 0 | Yes | No | V-2 |
| Example 9 | P-9 | P 2.12% | 0 | Yes | Yes | V-0 |
| Example 10 | P-10 | P 1.74% | 0 | No | No | V-0 |
| Control Ex. 1 | PN | 0 | 86 | Yes | No | V-2 |
| Control Ex. 2 | MPN | 0 | 42 | No | No | V-2 |
| Control Ex. 3 | TBBA | Br 34.4% | 0 | Yes | Yes | V-0 |

Tables 1, 2, and 3 show that the cured epoxy resins of the present invention have good mechanical and thermal properties, and have excellent flame retardant properties, especially no fume and dripping occur in the combustion test, and thus is very suitable for the printed circuit board applications. The glass transition temperatures (Tg) of the cured epoxy resins of the present invention are higher than that of the one cured with the conventional PN curing agent. In particular, those containing both the nitrogen and phosphorus elements which were cured with the melamine-phenol novolac type hardeners (P-2, ODOPM-MPN; P-8, DPPM-MPN; P-10, DPOM-MPN) not only have glass transition temperatures (Tg) 50–60° C. higher than that of the one cured with the conventional TBBA curing agent, but have good performance in thermal properties and char yield. These indicate that the nitrogen and phosphorus elements contained in the hardener of the present invention have a synergistic effect in flame-retardancy of the cured epoxy resin.

EXAMPLES 11~17

Cured epoxy resins were prepared from a cresol formaldehyde novolac epoxy resin (CNE) with the hardeners P'-1, P'-3 to P'-7, and P-9' prepared in Preparation Examples 22 to 28 in a 1:1 equivalent ratio and with 0.2 wt % of triphenylphosphine as a curing accelerator. The mixture was grounded into fine powders to give thermosettable epoxy resin powders. The resin powders were cured in a mold at 150° C. and 50 kg/cm$^2$ for a period of one hour and then at 170° C. for two hours and further postcured at 200° C. for three hours to obtain cured specimens.

The dynamic mechanical analysis (DMA) properties of the resulting cured epoxy resins prepared in Examples 11–17 are shown in Table 1A; the thermogravimetric analysis data thereof are shown in Table 2A; and the flame-retardant properties thereof are shown in Table 3A.

TABLE 1A

DMA properties

| Specimens | Hardener | Glass transition temperature (Tg, ° C.) | Flexural strength at 50° C. dyne/cm |
|---|---|---|---|
| Example 11 | P'-1 | 178 | 7.5 |
| Example 12 | P'-3 | 172 | 7.3 |
| Example 13 | P'-4 | 170 | 7.2 |
| Example 14 | P'-5 | 175 | 7.5 |
| Example 15 | P'-6 | 173 | 7.8 |
| Example 16 | P'-7 | 169 | 7.2 |
| Example 17 | P'-9 | 167 | 6.8 |
| Control Ex. 1 | PN | 167 | 6.8 |
| Control Ex. 3 | TBBA | 113 | 6.1 |

TABLE 2

TGA data

| Specimens | Hardener | Td 5% ° C. | Maximum thermal degradation temperature ° C. | Char yield (%) at 700° C. |
|---|---|---|---|---|
| Example 11 | P'-1 | 377 | 418 | 48 |
| Example 12 | P'-3 | 365 | 398 | 46 |
| Example 13 | P'-4 | 358 | 382 | 42 |
| Example 14 | P'-5 | 312 | 367 | 36 |
| Example 15 | P'-6 | 332 | 373 | 38 |
| Example 16 | P'-7 | 369 | 409 | 42 |
| Example 17 | P'-9 | 361 | 403 | 40 |
| Control Ex. 1 | PN | 417 | 479 | 35 |
| Control Ex. 3 | TBBA | 387 | 407 | 38 |

TABLE 3

Flame retardant properties (UL-94 test)

| Specimens | Hardener | Content of P or Br | Burning time Sec | Drip | Fume | Classification |
|---|---|---|---|---|---|---|
| Example 11 | P'-1 | P 2.12% | 0 | No | No | V-0 |
| Example 12 | P'-3 | P 2.61% | 0 | No | No | V-0 |
| Example 13 | P'-4 | P 3.48% | 0 | No | No | V-0 |
| Example 14 | P'-5 | P 3.45% | 0 | No | No | V-0 |
| Example 15 | P'-6 | P 3.14% | 0 | No | Slightly | V-0 |
| Example 16 | P'-7 | P 2.12% | 0 | No | No | V-0 |
| Example 17 | P'-9 | P 2.08% | 0 | No | No | V-0 |
| Control Ex. 1 | PN | 0 | 86 | Yes | No | V-2 |
| Control Ex. 3 | TBBA | Br 34.4% | 0 | Yes | Yes | V-0 |

The glass transition temperatures (Tg) of the cured epoxy resins of the present invention are not only higher than that of the one cured with the conventional PN curing agent, but also 50–60° C. higher than that of the one cured with the conventional TBBA curing agent as shown in Table 1A. Moreover, the data in Tables 1A, 2A and 3A show that the cured epoxy resins of the present invention have good mechanical and thermal properties, and have excellent flame retardant properties, especially no fume and dripping occur in the combustion test, and thus is very suitable for the printed circuit board applications.

IV. Using Phosphorus-containing Multi-functionality Phenol Novolac Resins P-1 and P'-1 as a Curing Agent for Epoxy Resin Various amounts of the hardeners P-1 and P'-1 were separately mixed with phenol formaldehyde novolac (PN) to form a mixed curing agent for cresol formaldehyde novolac epoxy resin (CNE) to determine the flame-retardant effect of phosphorus. The mixed curing agents consisting of P-1/PN in various weight ratios (0/100, 25/75, 50/50, 75/25, and 100/0) were prepared as well as the mixed curing agents P'-1/PN. Triphenyl phosphine (Ph$_3$P) powder was used as a curing accelerator. The CNE was mixed with the above mixed curing agents and 0.2 wt % Ph$_3$P in a mill at 25° C. to give thermosettable epoxy resin powders, wherein the equivalent ratio of epoxide group to hydroxyl group is 1:1. The resin powders were cured in a mould at 150° C. and 50 kg/cm$^2$ for a period of one hour and then at 170° C. for two hours and further postcured at 200° C. for three hours to obtain cured specimens.

V. Using Nitrogen-phosphosur-containing Multi-functionality Melamine-phenol Novolac Resin P-2 as a Curing Agent for Epoxy Resin Various amounts of the hardener P-2 were separately mixed with phenol formaldehyde novolac (PN) to form a mixed curing agent for cresol formaldehyde novolac epoxy resin (CNE) to determine the flame-retardant effect of phosphorus. The mixed curing agents consisting of P-2/PN in various weight ratios (0/100, 25/75, 50/50, 75/25, and 100/0) were prepared as well as the mixed curing agents P'-1/PN. Triphenyl phosphine (Ph$_3$P) powder was used as a curing accelerator. The CNE was mixed with the above mixed curing agents and 0.2 wt % Ph$_3$P in a mill at 25° C. to give thermosettable epoxy resin powders, wherein the equivalent ratio of epoxide group to hydroxyl group is 1:1. The resin powders were cured in a mould at 150° C. and 50 kg/cm$^2$ for a period of one hour and then at 170° C. for two hours and further postcured at 200° C. for three hours to obtain cured specimens.

For comparison, various weight ratios of tetrabromobisphenol A (TBBA) and PN (25/75, 50/50, 75/25, 100/0) were also used as a curing agent to prepare the cured specimens as above.

The cured specimens were subjected to the thermogravimetric analysis and the UL-94 test. The results are shown in Table 4 and Table 5.

It can be seen from Table 4 that the Tg values of the phosphorus-containing cured epoxy resin specimens of the present invention (P-1/PN and P'-1/PN) are about 40° C. higher than those of the conventional bromine-containing cured epoxy resin specimens; and are about 70° C. higher for the nitrogen-phosphorus-containing cured epoxy resin specimens of the present invention (P-2/PN). Furthermore, both the phosphorus-containing and nitrogen-phosphorus-containing cured epoxy resin specimens of the present invention exhibit higher thermal degradation temperatures and higher char yields in comparison with the conventional bromine-containing cured epoxy resin specimens The data in Table 5 show that 1% phosphorus content of the phosphorus-containing cured epoxy resin of the present invention can produce substantially the same flame-retardant effect as 7~10% bromine content of the conventional bromine-containing cured epoxy resin. In particular, a less phosphorus content of the nitrogen-phosphorus-containing cured epoxy resin of the present invention is needed to exhibit the same flame-retardant effect due to the synergistic effect resulting from nitrogen and phosphorus elements. In addition, both the phosphorus-containing and the nitrogen-phosphorus-containing cured epoxy resin specimens of the present invention generate much less fumes in the combustion test.

The results shown in Tables 4 and 5 indicate that both the phosphorus-containing and the nitrogen-phosphorus-containing cured epoxy resin of the present invention is very suitable for semiconductor encapsulation and printed circuit board applications.

TABLE 5

| Specimens | | UL-94 test Burning time | | |
|---|---|---|---|---|
| P-1/PN | P % | (Sec) | Fume | Classification |
| 0/100 | 0 | 86 | − | V-2 |
| 25/75 | 0.52 | 36 | -- | V-2 |
| 50/50 | 0.98 | 16 | -- | V-1 |
| 75/25 | 1.42 | 0 | -- | V-0 |
| 100/0 | 1.75 | 0 | -- | V-0 |
| P'-1/PN | P % | | | |
| 0/100 | 0/0 | 86 | − | V-2 |
| 25/75 | 0.51/1.39 | 26 | -- | V-1 |
| 50/50 | 0.96/2.61 | 6 | -- | V-0 |
| 75/25 | 1.36/3.70 | 0 | -- | V-0 |
| 100/0 | 1.73/4.69 | 0 | -- | V-0 |
| P-2/PN | P %/N % | | | |
| 0/100 | 0/0 | 42 | − | V-2 |
| 25/75 | 0.51/1.39 | 18 | | V-1 |
| 50/50 | 0.96/2.61 | 0 | | V-0 |
| 75/25 | 1.36/3.70 | 0 | | V-0 |
| 100/0 | 1.73/4.69 | 0 | | V-0 |
| TBBA/PN | Br % | | | |
| 25/75 | 5.8 | 18 | ++ | V-1 |
| 50/50 | 12.9 | <1 | ++ | V-0 |
| 75/25 | 22.1 | 0 | + | V-0 |
| 100/0 | 34.4 | 0 | − | V-0 | a) ++: heavy;
+: slightly;
−: scarcely;
--: no fume.

VI. The Preparation of a Cured Epoxy Resin from an Advanced Epoxy Resin with the Phosphorus-containing Multi-functionality Phenol Novolac Resins P-1 and P'-1, and the Nitrogen-phosphorus-containing Multi-Functionality Melamine-phenol Novolar Resin P-2 as a Curing Agent Cured epoxy resins were prepared from the advanced epoxy resin Epikote 1001 (EEW 450–500; purchased from

TABLE 4

TGA data

| Specimens mixed curing agent (ratio) | Tg (° C.) | Temperature of 5 wt % loss, ° C. | | Temperature of 10 wt % loss, ° C. | | Rapid rate Tr (° C.) | | | | Char yield at 700° C., (%) | |
|---|---|---|---|---|---|---|---|---|---|---|---|
| | | | | | | Step 1 | Step 1 | Step 2 | Step 2 | | |
| | | Air | N₂ | Air | N₂ | Air | N₂ | Air | N₂ | Air | N₂ |
| P-1/PN (0/100) | 167 | 433 | 417 | 453 | 437 | 470 | 479 | — | — | 27 | 30 |
| P-1/PN (25/75) | 169 | 421 | 407 | 437 | 423 | 450 | 435 | 638 | — | 30 | 42 |
| P-1/PN (50/50) | 171 | 417 | 401 | 431 | 417 | 442 | 437 | 617 | 601 | 33 | 44 |
| P-1/PN (75/25) | 175 | 413 | 391 | 427 | 413 | 437 | 427 | 584 | 572 | 35 | 45 |
| P-1/PN (100/0) | 178 | 407 | 383 | 423 | 407 | 431 | 421 | 580 | 566 | 38 | 47 |
| P-2/PN (0/100) | 181 | 453 | 429 | 470 | 457 | 489 | 497 | — | — | 30 | 35 |
| P-2/PN (25/75) | 185 | 449 | 421 | 461 | 453 | 483 | 487 | 658 | — | 32 | 44 |
| P-2/PN (50/50) | 189 | 437 | 417 | 457 | 447 | 477 | 475 | 632 | 627 | 36 | 45 |
| P-2/PN (75/25) | 192 | 431 | 411 | 449 | 439 | 471 | 463 | 618 | 623 | 39 | 47 |
| P-2/PN (100/0) | 196 | 423 | 409 | 443 | 435 | 465 | 457 | 607 | 597 | 41 | 49 |
| P'-1/PN (0/100) | 167 | 433 | 417 | 453 | 437 | 470 | 479 | — | — | 27 | 30 |
| P'-1/PN (25/75) | 169 | 407 | 403 | 420 | 423 | 450 | 443 | 610 | — | 41 | 43 |
| P'-1/PN (50/50) | 171 | 403 | 387 | 417 | 417 | 442 | 437 | 606 | 601 | 43 | 45 |
| P'-1/PN (75/25) | 175 | 383 | 379 | 425 | 397 | 423 | 422 | 573 | 566 | 44 | 46 |
| P'-1/PN (100/0) | 178 | 379 | 377 | 407 | 395 | 421 | 418 | 580 | 562 | 46 | 48 |
| TBBA/PN (25/75) | 146 | 293 | 401 | 349 | 413 | 355 | 417 | — | — | 22 | 34 |
| TBBA/PN (50/50) | 135 | 383 | 392 | 387 | 397 | 397 | 401 | — | — | 23 | 35 |
| TBBA/PN (75/25) | 126 | 377 | 386 | 385 | 393 | 393 | 397 | — | — | 24 | 36 |
| TBBA/PN (100/0) | 113 | 383 | 387 | 397 | 401 | 403 | 407 | — | — | 26 | 38 |

Shell Co.) with the hardeners P-1 (ODOPM-PN), P'-1 (ODOPC-PN) and P-2 (ODOPM-MPN).

The advanced epoxy resin was heated to 150° C. and mixed with the hardener (1:1 equivalent ratio) in a molten state while stirring, and then poured into a hot aluminum mould, cured in an oven at 170° C. for one hour, and then postcured at 200° C. for two hours.

For comparison, phenol-formaldehyde novolac (PN) and tetrabromobisphenol A (TBBA) were also used as a curing agent to prepare the cured specimens as above.

The cured specimens were subjected to the thermogravimetric analysis and the UL-94 test. The results are shown in Table 6 and Table 7.

It can be seen from Table 6 that the Tg values of the cured epoxy resin specimens prepared with-the phosphorus-containing hardeners of the present invention P-1 (ODOPM-PN) and P'-1 (ODOPC-PN) are about 8–12° C. higher than that cured with the conventional bromine-containing curing agent, tetrabromobisphenol A (TBBA); and are about 20° C. higher for the cured epoxy resin prepared with the nitrogen-phosphorus-containing hardener of the present invention P-2 (ODOPM-MPN). Furthermore, both the phosphorus-containing and nitrogen-phosphorus-containing cured epoxy resin specimens of the present invention exhibit higher thermal degradation temperatures and higher char yields in comparison with the conventional bromine-containing cured epoxy resin specimens The data in Table 7 show that 1% or less phosphorus content of the phosphorus-containing cured epoxy resin of the present invention can produce substantially the same flame-retardant effect as 7~10% bromine content of the conventional bromine-containing cured epoxy resin. In addition, both the phosphorus-containing and the nitrogen-phosphorus-containing cured epoxy resin specimens of the present invention generate much less fumes in the combustion test. The results shown in Tables 6 and 7 indicate that both the phosphorus-containing and the nitrogen-phosphorus-containing cured epoxy resin of the present invention is very suitable for semiconductor encapsulation and printed circuit board applications.

TABLE 7

UL-94 test

| Hardener | Flame-retardant element (%) | Average burning time (Sec) | Fume | Drip | Classification |
|---|---|---|---|---|---|
| PN | No | 87 | -- | Yes | V-02 |
| TBBA | Br (17.27%) | <1 | ++ | Yes | V-0 |
| P-1 | P (2.19%) | 0 | -- | No | V-0 |
| P-2 | P (1.55%)/N (2.09%) | 2 | -- | No | V-0 |
| P'-1 | P (2.15%) | 0 | -- | No | V-0 |

++: heavy
--: No

The presently disclosed embodiments are therefore considered in all respects to be illustrative and not restrictive. The scope of the invention is indicated by the appended claims rather than the foregoing description, and all changes that come within the meaning and range of equivalents thereof are intended to be embraced therein.

The invention claimed is:

1. A cured phosphorus-containing epoxy resin prepared by cross-linking an epoxy resin or an advanced epoxy resin in a molten state of said epoxy resin or an advanced epoxy resin and in the presence of a hardener having a formula selected from the group consisting of (a), (b), (c) and (d):

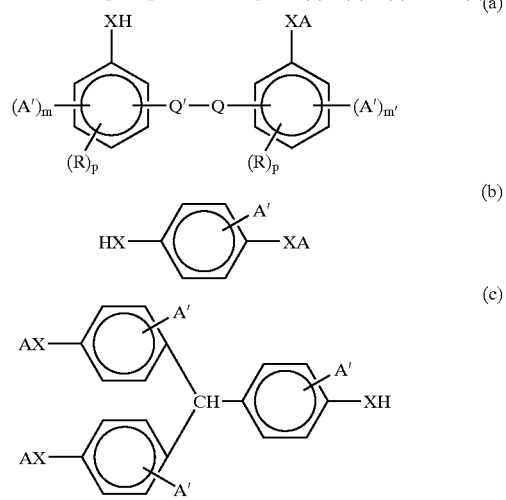

TABLE 6

TGA data

| | Specimens | | | | | | | | | | | |
| | Amount of hardener (g/equivalent) | Amount of advanced epoxy resin (g/equivalent) | Tg (° C.) | Temperature of 5 wt % loss, ° C. | | Temperature of 10 wt % loss, ° C. | | Rapid rate Tr (° C.) | | | | Char yield at 700° C, (%) | |
| Hardener | | | | Air | $N_2$ | Air | $N_2$ | Stpe 1 Air | Step 1 $N_2$ | Step 2 Air | Step 2 $N_2$ | Air | $N_2$ |
|---|---|---|---|---|---|---|---|---|---|---|---|---|---|
| PN | 10.5/0.106 | 50/0.105 | 112 | 377 | 421 | 413 | 437 | 449 | 466 | — | — | 5 | 14 |
| TBBA | 10.4/0.106 | 50/0.106 | 124 | 361 | 363 | 365 | 367 | 386 | 380 | — | — | 10 | 23 |
| P-1 | 10.4/0.105 | 50/0.105 | 132 | 377 | 373 | 409 | 397 | 439 | 437 | 687 | 616 | 21 | 27 |
| P-2 | 10.4/0.105 | 50/0.105 | 146 | 383 | 379 | 421 | 413 | 448 | 445 | 751 | 618 | 29 | 34 |
| P'-1 | 10.4/0.105 | 50/0.105 | 136 | 377 | 367 | 401 | 391 | 436 | 433 | 742 | 606 | 26 | 29 |

—: Step 2 of rapid rate was not found

-continued

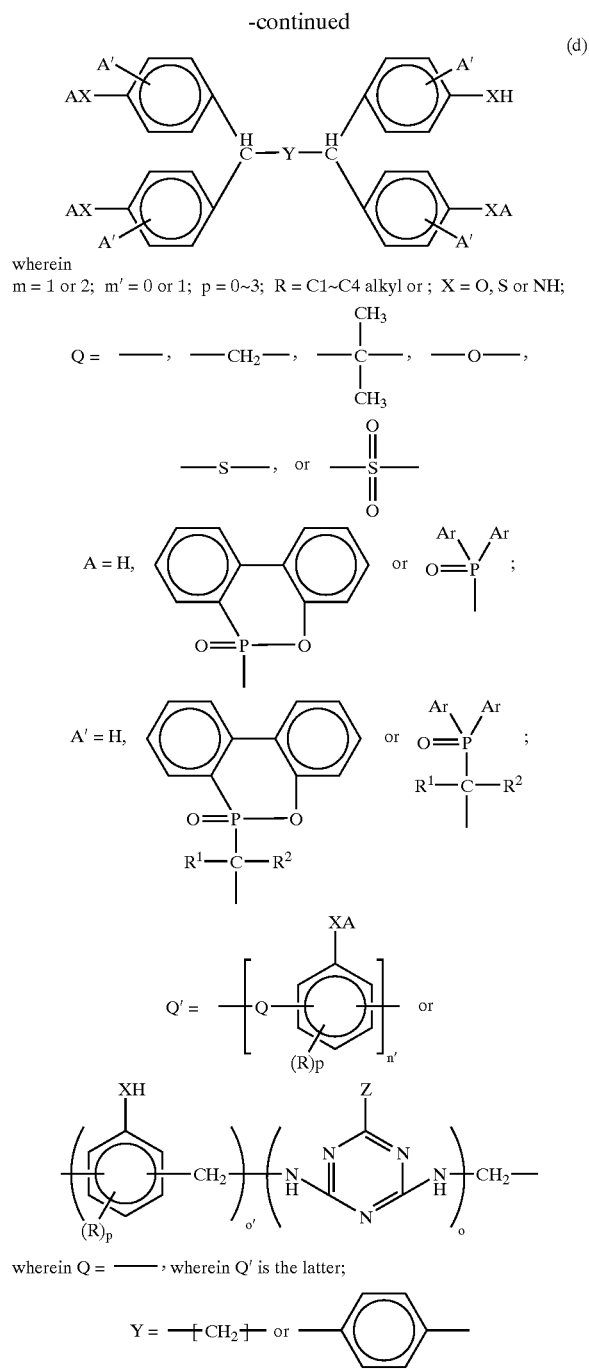

wherein
m = 1 or 2; m' = 0 or 1; p = 0~3; R = C1~C4 alkyl or ; X = O, S or NH;

wherein Q = ——; wherein Q' is the latter;

Y = —(CH$_2$)$_r$— or —⌬— wherein
R$^1$, R$^2$ independently are H, C1~C18 alkyl, C6~C18 aryl, C6~C18 substituted aryl, C6~C18 aryl methylene, or C6~C18 substituted aryl methylene;

n'=0~11; Z=—NH$_2$, —NHR, or —R; o=1~3; o'=3~10; r=0~6; R, Q and p are defined as above;

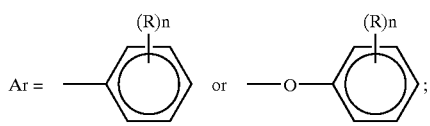

wherein R is defined as above and n=0–5;

wherein either all the A or all the A' in each formula of (a) to (d) are H, and at least one of the A is not H when all the A' are H in each formula of (a) to (d), and at least one of the A' is not H when all the A are H in each formula of (a) to (d);

or a hardener mixture comprising one said hardener having said formula and an additional different hardener for epoxy resin.

2. The cured phosphorus-containing epoxy resin according to claim 1 having 0.5–30% of phosphorus based on the weight of the cured phosphorus-containing epoxy resin.

3. The cured phosphorus-containing epoxy resin according to claim 2 having 0.5–5% of phosphorus based on the weight of the cured phosphorus-containing epoxy resin.

4. The cured phosphorus-containing epoxy resin according to claim 1, wherein said epoxy resin is a bi-functional epoxy resin selected from the group consisting of bisphenol A, bisphenol F, bisphenol S, and biphenol epoxy resins; a multi-functional epoxy resin of phenol formaldehyde novolac epoxy resin or cresol formaldehyde novolac epoxy resin and; a mixture of the bi- functional epoxy resin and the multi-functional epoxy resin.

5. The cured phosphorus-containing epoxy resin according to claim 1, wherein the hardener has a structure wherein all the A' are H and

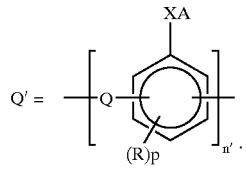

6. The cured phosphorus-containing epoxy resin according to claim 5, wherein the hardener has a structure of the formula (a).

7. The cured phosphorus-containing epoxy resin according to claim 1, wherein the hardener has a structure of the formula (b), and all the A' are H.

8. The cured phosphorus-containing epoxy resin according to claim 1, wherein the hardener has a structure of the formula (c), and all the A' are H.

9. The cured phosphorus-containing epoxy resin according to claim 1, wherein the hardener has a structure of the formula (d), and all the A' are H.

10. The cured phosphorus-containing epoxy resin according to claim 1, wherein all the A are H, and Q' is

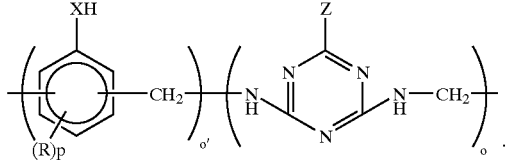

11. The cured phosphors-containing epoxy resin according to claim 10, wherein the hardener has a structure of the formula (a).

12. The cured phosphorus-containing epoxy resin according to claim 1, wherein the hardener has a structure of the formula (b) and all the A are H.

13. The cured phosphorus-containing epoxy resin according to claim 1, wherein the hardener has a structure of the formula (c) and all the A are H.

14. The cured phosphorus-containing epoxy resin according to claim 1, wherein the hardener has a structure of the formula (d) and all the A are H.

* * * * *